United States Patent [19]
Wilson

[11] Patent Number: 5,482,513
[45] Date of Patent: Jan. 9, 1996

[54] ANKLE JOINT WITH DEDICATED TRANSVERSE ROTATOR

[76] Inventor: Michael T. Wilson, 3131 Villa La., Missouri City, Tex. 77459

[21] Appl. No.: 134,384

[22] Filed: Oct. 12, 1993

Related U.S. Application Data

[63] Continuation-in-part of Ser. No. 40,905, Mar. 31, 1993.

[51] Int. Cl.[6] ........................................... A61F 2/66
[52] U.S. Cl. .................... 623/52; 623/47; 623/53
[58] Field of Search .................. 623/55, 53, 52, 623/47, 48–51, 54

[56] References Cited

U.S. PATENT DOCUMENTS

| | | | |
|---|---|---|---|
| 409,311 | 8/1889 | Snyder | 623/53 X |
| 419,019 | 1/1890 | Kolbe | 623/54 X |
| 1,071,230 | 8/1913 | Hanger | 623/54 X |
| 1,294,632 | 2/1919 | Dickson . | |
| 2,731,645 | 1/1956 | Woodall | 623/53 |
| 3,196,463 | 7/1965 | Farneth | 623/49 |
| 3,940,804 | 3/1976 | Benton et al. | 623/50 X |
| 4,328,594 | 5/1982 | Campbell et al. . | |
| 4,446,580 | 5/1984 | Furuya et al. | 623/53 |
| 4,461,045 | 7/1984 | Shorter et al. . | |
| 4,463,459 | 8/1984 | Shorter et al. . | |
| 4,547,913 | 10/1985 | Phillips | 623/27 |
| 4,645,509 | 2/1987 | Poggi et al. | 623/55 |
| 4,721,510 | 1/1988 | Cooper et al. | 623/55 |
| 4,822,363 | 4/1989 | Phillips | 623/27 |
| 4,892,554 | 1/1990 | Robinson | 623/55 |
| 5,030,239 | 7/1991 | Copes | 623/52 |
| 5,112,356 | 5/1992 | Harris et al. | 623/49 |
| 5,158,570 | 10/1992 | Schey et al. | 623/52 |
| 5,258,038 | 11/1993 | Robinson et al. | 623/49 |
| 5,376,140 | 12/1994 | Ryan | 623/55 |

FOREIGN PATENT DOCUMENTS

| | | | |
|---|---|---|---|
| 0227290 | 1/1925 | United Kingdom | 623/53 |
| 2070439 | 9/1981 | United Kingdom | 623/47 |
| 2092451 | 8/1982 | United Kingdom | 623/53 |
| 8800815 | 2/1988 | WIPO | 623/53 |

OTHER PUBLICATIONS

Flex–Foot, Inc. flyers entitled, "Something Revolutionary Is In The Air," Adjust the foot, not the lifestyle, Engineered For The Long Run, Simply Precise, Engineered Flexibility, Designed For A Growing Market, Amputee Profile (Mary Jane Gardner), Amputee Profile (Dan Broome), and Flex–Foot, Inc. Newsletter, Issue No. 4, 1992.
Otto Bock flyer, "1M1—Otto Bock Multiaxial Foot".
Campbell–Childs, Inc. brochure and flyer entitled, "The All New 'Sportsmen' S.A.F.E. II".
Devcon instruction sheet on "Flexane® Urethane".
Boston Gear catalogue, Self-Aligning Bearings, p. D68.
Hosmer, The Quantum Foot—Brochure.
Campbell–Childs, Inc. Stationary Attachment Flexible Endoskeleton II Mailer, Jul. 1989.
Campbell–Childs, Inc.–S.A.F.E. Prosthetic Foot Catalog.
United States Manufacturing Company—Multiplex Brochure.
The Ohio Willow Wood Co., Step into the Future with the Carbon Copy II Energy Storing Foot.
Footnotes (Flex–Foot)—Mailer, Mar. 1989.
Flex–Foot, Inc.—Price List.

*Primary Examiner*—David H. Willse
*Attorney, Agent, or Firm*—Conley, Rose & Tayon

[57] ABSTRACT

A lightweight foot prosthesis is claimed, having a foot, an ankle joint connected to the foot and capable of motion about a transverse axis, forward and rear snubbers for limiting rotation of the ankle joint, and a connector for connecting the ankle joint to a leg. The ankle joint preferably comprises a body having a bore, and a shell having an integral axle, with the axle extending pivotally through the bore.

16 Claims, 8 Drawing Sheets

ANKLE JOINT WITH DEDICATED TRANSVERSE ROTATOR

This is a continuation-in-part of application Ser. No. 08/040,905 filed on Mar. 31, 1993.

TECHNICAL FIELD OF THE INVENTION

The present invention relates to the foot section of an artificial leg and more particularly to a prosthetic foot specifically designed for geriatric users and others who require less massive prostheses. Still more particularly, the present invention relates to construction of a prosthetic foot and ankle joint adapted to provide a desired degree of mobility without excessive bulk.

BACKGROUND OF THE INVENTION

Prosthetic feet are well known in the art, and several such feet have been designed to accomplish one or more objectives.

A useful prosthesis will simulate the operation and motion of an anatomical foot to a desired degree. An anatomical foot, including the ankle joint, is capable of motion around three perpendicular axes, as well as varying degrees of flexure. Specifically, the anatomical foot and ankle are capable of dorsiflexion, planiflexion, inversion, eversion, and transverse rotation. Dorsiflexion and planiflexion comprise the movement up and down of the ball of the foot with respect to the heel that occurs during a normal forward step. Inversion and eversion are the twisting of the foot around its longitudinal axis, resulting in outward and inward tilting of the ankles, respectively. Transverse rotation occurs when the foot rotates with respect to the longitudinal axis of the leg, such as occurs during left and right turns of the body.

Known foot prostheses include commercial feet that are capable of all three types of rotation. Typically, however, the joints capable of such complicated motion require bulky moving parts and are generally far too heavy for geriatric or very young patients, or other patients who suffer some degree of muscular weakness. Furthermore, some patients may not require high degree of flexibility, and may even desire the increased stability associated with a prosthesis that is capable of rotation about a single axis. Such a prosthesis would allow dorsiflexion and planiflexion, but not inversion, eversion, or transverse rotation. This would permit a near-normal step during forward motion, and would reduce the likelihood that the wearer might lose his or her balance as a result of uncontrolled or unintended rotation about one of the other axes.

In addition, it is desirable for a foot prosthesis to be capable of absorbing, storing, and releasing energy, so that the prosthesis returns itself to a relaxed, unflexed position when the moving force is removed. Prostheses that are designed for use during athletic activities, such as running or playing basketball, are particularly efficient at energy storage and return, providing a springy step. Such energy storage is typically accomplished by the inclusion of coil springs or other reciprocating means which absorb energy on flexure and release it efficiently upon removal of the applied force. The energy-storing components that are typically used for efficient energy return can contribute significantly to the weight of the prosthesis.

In contrast, older, less mobile wearers neither need nor want a high degree of return of stored energy. Instead, it is preferable for the prostheses worn by these wearers to absorb and dissipate a portion of the energy of each flexion while retaining sufficient energy to return the prosthesis to its unflexed position. This provides a more stable, cushioned step, and reduces the shock experienced by both the wearer and the prosthesis at each step.

Finally, it is necessary that a foot prosthesis be strong enough to support its wearer and durable enough to withstand the stresses of repeated stepping motions over long periods of time. Conventional prostheses tend to be designed for maximize strength, at the cost of added bulk and weight, making them unsuitable for geriatric or very young wearers, who do not subject their prostheses to the same loads as the average wearer.

Hence it is desired to provide a flexible, durable prosthesis that provides a slightly damped step and requires a minimal mass.

SUMMARY OF THE INVENTION

The present invention comprises a foot prosthesis having a light-weight foot portion and an attached light-weight ankle portion capable of a desired degree of rotation around a single axis. As used herein, the words "prosthesis" or "foot prosthesis" will refer to both the foot portion of a prosthetic foot and the ankle joint attached thereto.

Simplified construction of the foot and joint mechanisms enables the present invention to be at least about 50% lighter than typical foot prostheses. The foot portion of the prosthesis includes an integral instep and sole constructed of light weight polymeric material and is designed to provide support and flexure without added weight. The ankle portion of the prosthesis includes a single transverse joint that provides desired flexibility and stability without excess mass. The present joint allows dorsiflexion and planiflexion, but provides extra stability by avoiding flexibility with respect to other types of rotation. Other objects and advantages of the present invention will appear from the following description.

BRIEF DESCRIPTION OF THE DRAWINGS

For a detailed description of a preferred embodiment of the invention, reference will now be made to the accompanying drawings wherein.

DETAILED DESCRIPTION OF THE INVENTION

The present invention comprises a lightweight foot portion, an ankle joint affixed to said foot, such that the foot is capable of motion around at least one axis, means for limiting rotation of said ankle joint and means for connecting said ankle joint to a leg. The foot portion includes a naturally-shaped foot having a dorsal surface and a plantar surface and comprising a heel, a toe and a raised instep.

Referring initially to FIGS. 1–4, the prosthetic foot 10 of the present invention includes a foot 20, an attached ankle joint 30, and a connector 40. A prosthetic shin, or leg, which would normally be attached to connector 40 via a conventional connection is shown in phantom extending upward from connector 40 in FIG. 1. For purposes of discussion, the x, y, and z axes, about which an anatomical foot can rotate, are shown and have been assigned as follows. The x axis is perpendicular to both the leg and foot, passing through the sides of the ankle. The y axis is perpendicular to the leg and parallel to the foot, and the z axis is parallel to the leg.

Figure 1:
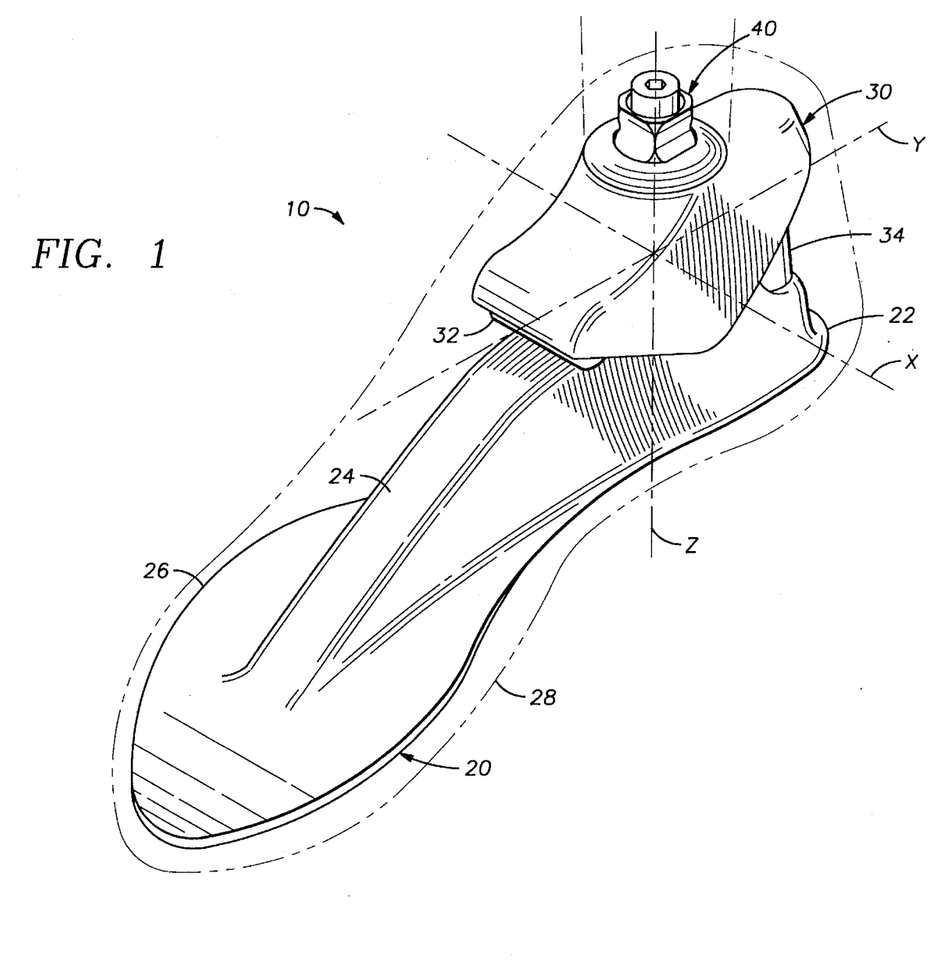
FIG. 1 is a perspective view of the prosthetic foot of the present invention wherein the surrounding cosmesis is shown in phantom.
Figure 2:
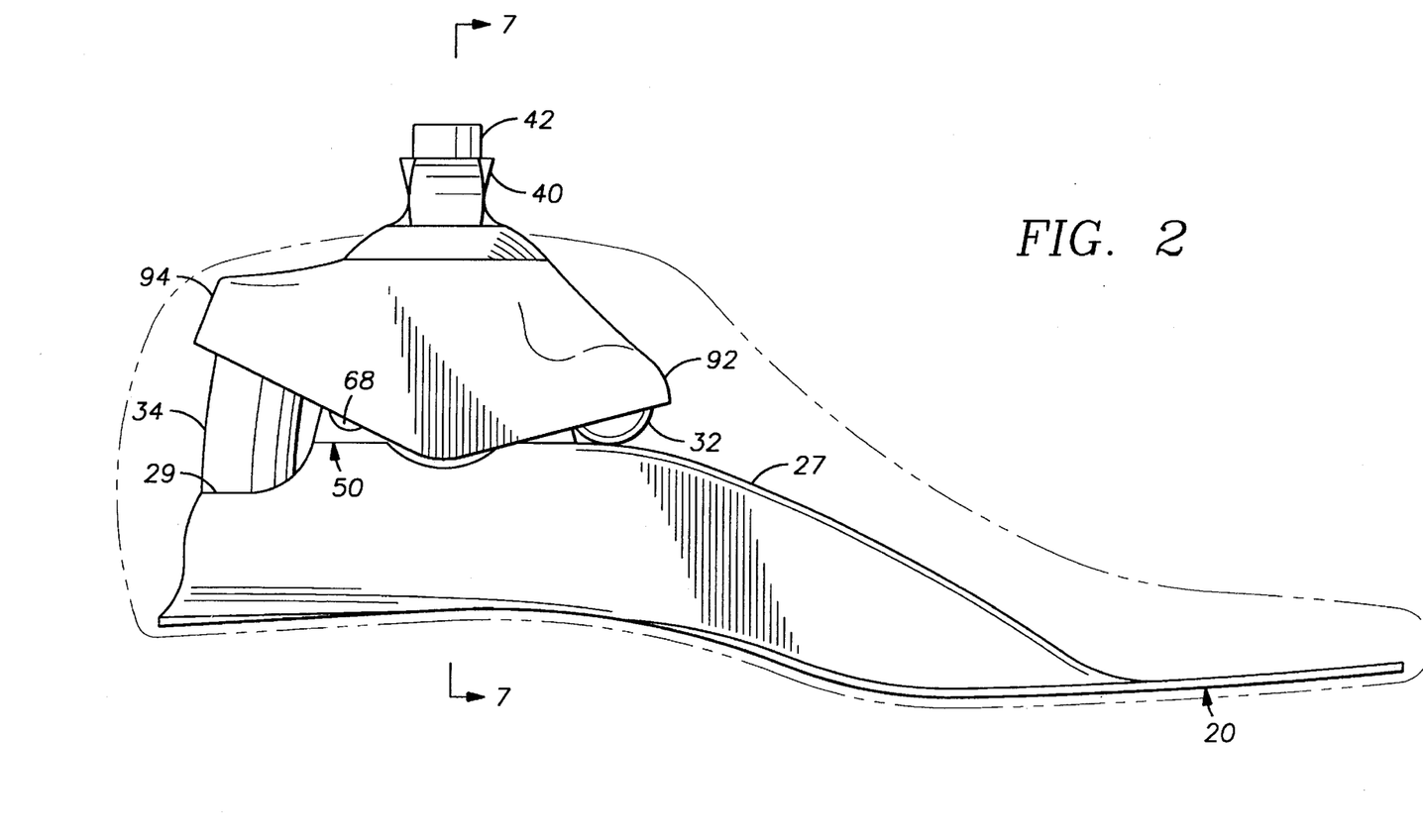
FIG. 2 is a side elevational view of the prosthetic foot of FIG. 1.
Figure 3:
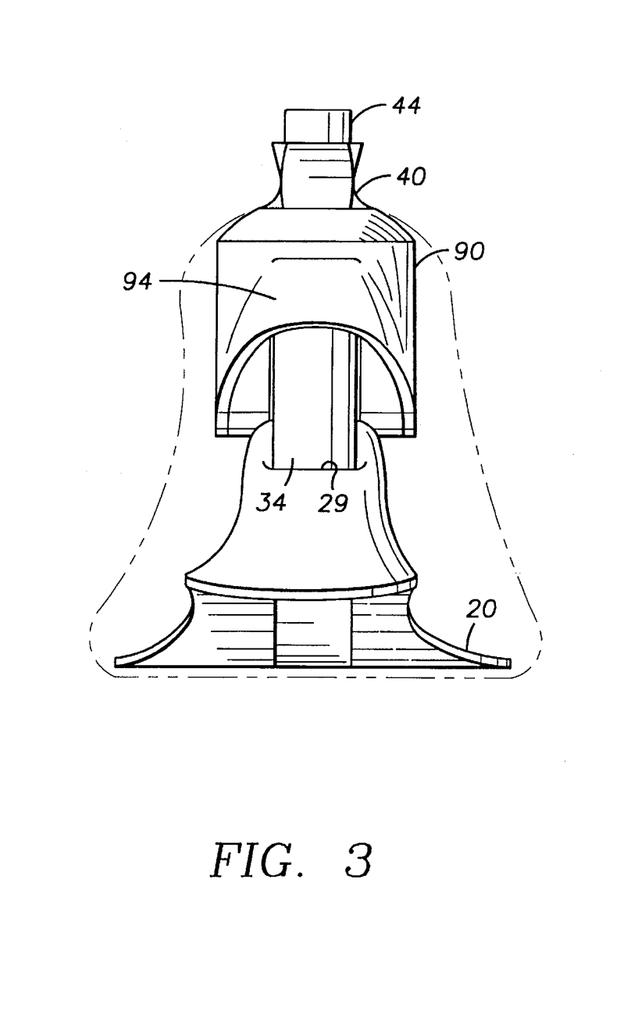
FIG. 3 is a rear elevational view of the prosthetic foot of FIG. 1.

Referring particularly to FIG. 1, foot 20 comprises a heel 22, a raised instep 24, and a substantially flat toe portion 26. Together, the heel, instep and toe 22, 24, 26 form a foot that closely replicates the structure and form of an anatomical foot. FIG. 1 also shows in phantom a cosmesis 28, which is molded around prosthetic foot 10. Cosmesis 28 is preferably constructed of foamed polyethylene.

It is preferred that the x axis, about which joint 30 is designed to rotate, be positioned at approximately twenty-five to thirty percent (25–30%) of the distance from heel 22 to toe 26. In addition, it is preferred that the transition from instep 24 to toe 26 occur at approximately seventy-five percent (75%) of the distance from heel 22 to toe 26.

Foot portion 20 is preferably constructed of a molded copolymer comprising approximately 100% polypropylene. It has been found that this polymer avoids an excessive level of creep and provides sufficient resilience for the present application. Other materials having suitable physical properties may be substituted for these polymers without departing from the spirit of the invention. Foot portion 20 is preferably formed by molding a working piece of the copolymer around a rigid model having a desired shape. It has been found advantageous to at least partially evacuate a region adjacent to the model. This allows the surrounding atmosphere outside the working piece to apply isostatic pressure to the piece, thereby causing it to conform smoothly and completely to the form. Alternatively foot portion 20 may be injection molded. For lightness, the molded underside (not shown) of raised instep 24 may include a hollow recess, as discussed in greater detail below.

Referring again to FIGS. 1–4, a forward snubber 32 and a rear snubber 34 are interposed between foot portion 20 and ankle joint 30 as discussed in greater detail below. Snubbers 32 and 34 comprise cylindrical resilient members and are preferably constructed of rubber, neoprene, high density urethane, or the like. A preferred material for the construction of snubbers 32, 34 is a polyurethane sold under the registered trademark Flexane® and manufactured by ITW Devcon, 30 Endicott St., Danvers, Mass. 01923.

Figure 4:
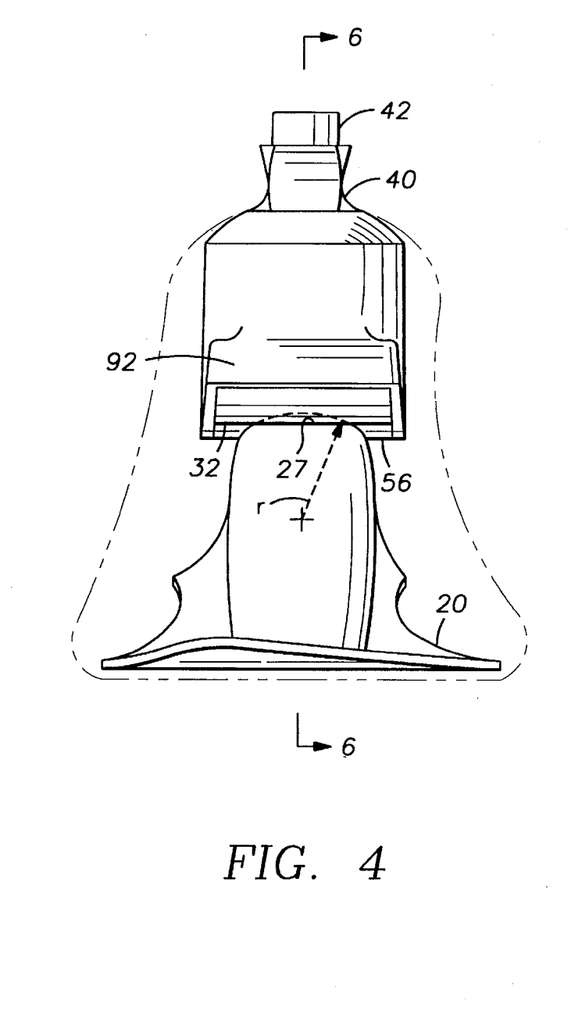
FIG. 4 is a front elevational view of the prosthetic foot of FIG. 1.
Figures 5, 5A:
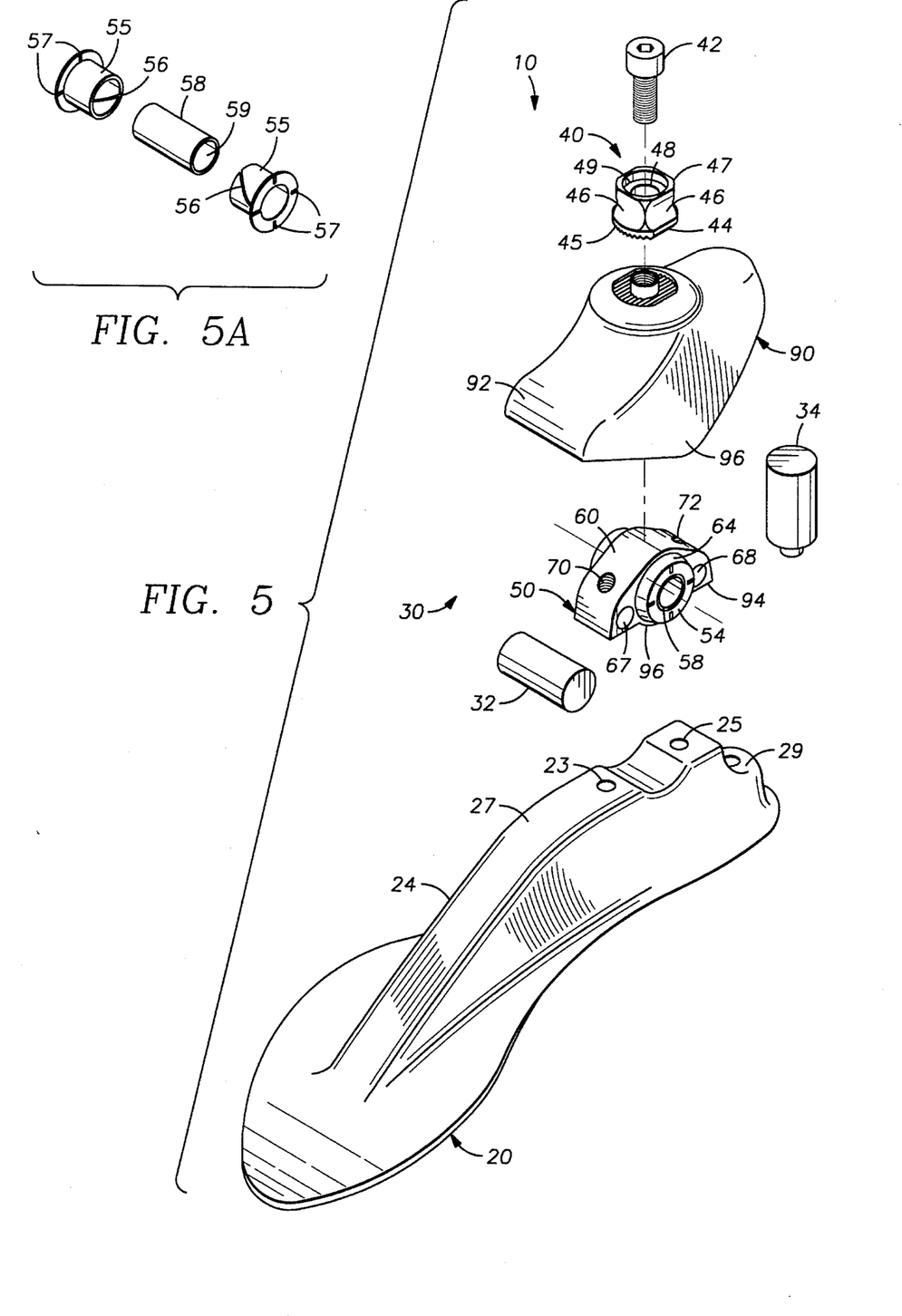
FIG. 5 is an exploded view of the prosthetic foot of FIG. 1 without the cosmesis.
FIG. 5A is an exploded view of the internal components of the ankle joint of FIG. 5.

Referring now to FIG. 5, the components of prosthesis 10 are shown in exploded form. Instep 24 includes a forward vertical bore 23 and a rear vertical bore 25 therethrough. Instep 24 further includes a curved front contact surface 27 and a planar rear contact surface 29 on its upper, or dorsal surface. As best shown in FIG. 4, contact surface 27 has a radius of curvature r. Still referring to FIG. 5, ankle joint 30 comprises a body 50, a liner 54, a tubular bearing 58 and a shell 90. Shell 90 includes a forward cup 92, a rear cup 94 and a pair of side portions 96. Shell 90 is connected to and surrounds body 50, liner 54 and bearing 58 by means of an integral axle 62, as described in detail below.

Referring now to FIGS. 5, 5A, 6 and 7, body 50 includes an oblong housing 60 in which liner 54 is transversely mounted, i.e., parallel to the x axis. Each side of housing 60 includes raised annular bevel 64 centered on the x axis. Bevel 64 contributes to the stability of the joint by allowing axle 62 to be slightly longer than the width of body 60.

As best seen in FIG. 5A, liner 54 preferably comprises a pair of identical ranged tubes 55 within body 50, tubes 55 are positioned so that their unflanged ends abut to form liner 54, which spans the width of housing 60 at bevel 64. According to the preferred embodiment, each tube 55 includes an expansion opening 56 along its entire length and a plurality of radial slots 57 at the outer edge of the flange. Tubes 55 are preferably constructed from nylon or other suitable polymer, and may be purchased under the trademark Nyliner, sold by Seastrom Manufacturing Company, Inc., 701 Sonora Ave., Glendale, Calif. 91201-2495.

Liner 54 is sized to receive bearing 58 coaxially, with the inner surface of tubes 55 adjacent the outer surface of bearing 58, such that bearing 58 also lies on the x axis within body 50. Bearing 58 has an inner surface 59 and is preferably any suitable brass tubing. For example, a suitable tubing has an outside diameter of 0.50 inches and an inside diameter of 0.45, such as is commonly commercially available. Other materials may be used for liner 54 and bearing 58, so long as they are capable of providing a bearing surface at the liner/bearing interface and are suitable for use in the present application.

Figure 6:
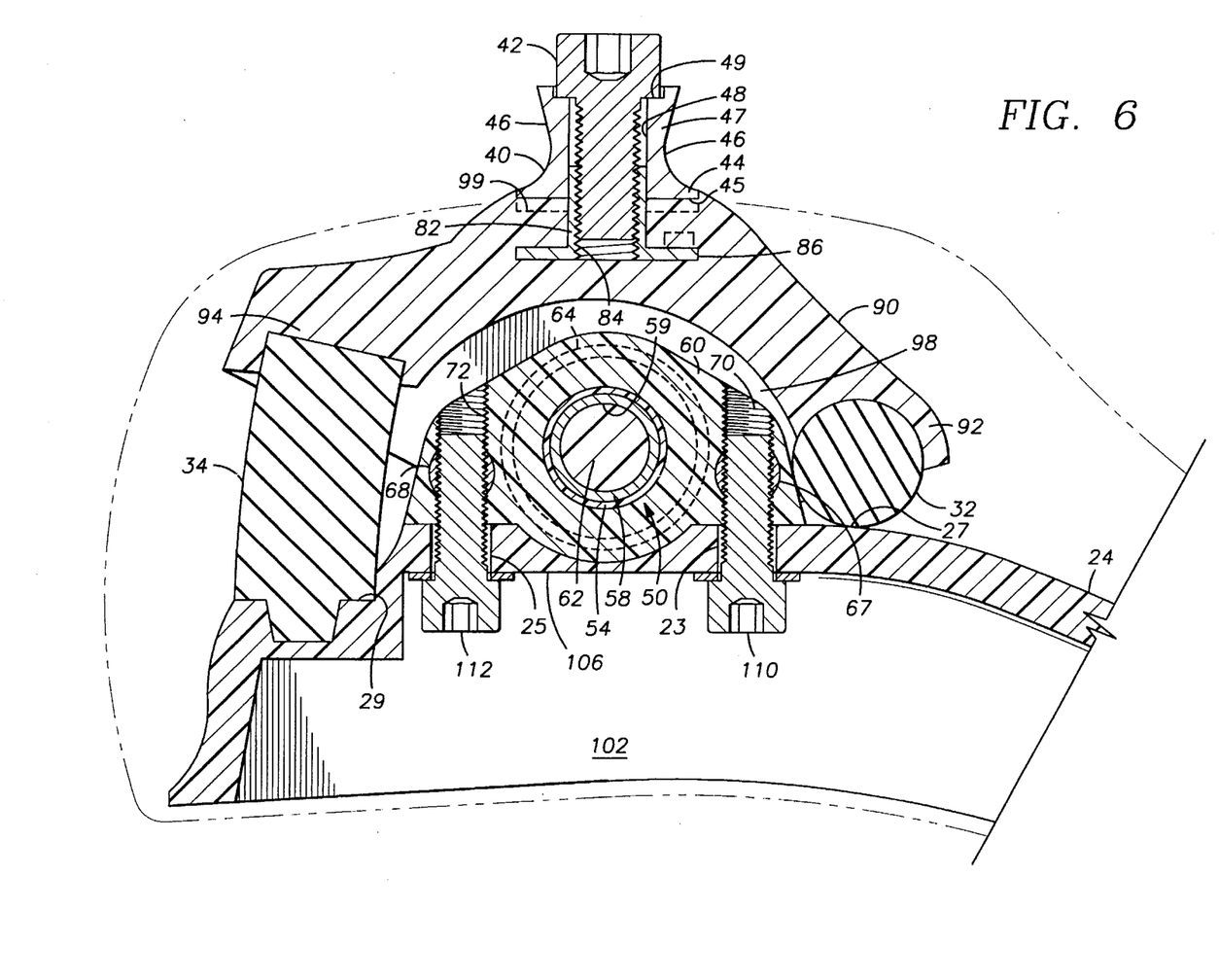
FIG. 6 is a cross-sectional view taken along lines 6—6 of FIG. 4.
Figure 7:
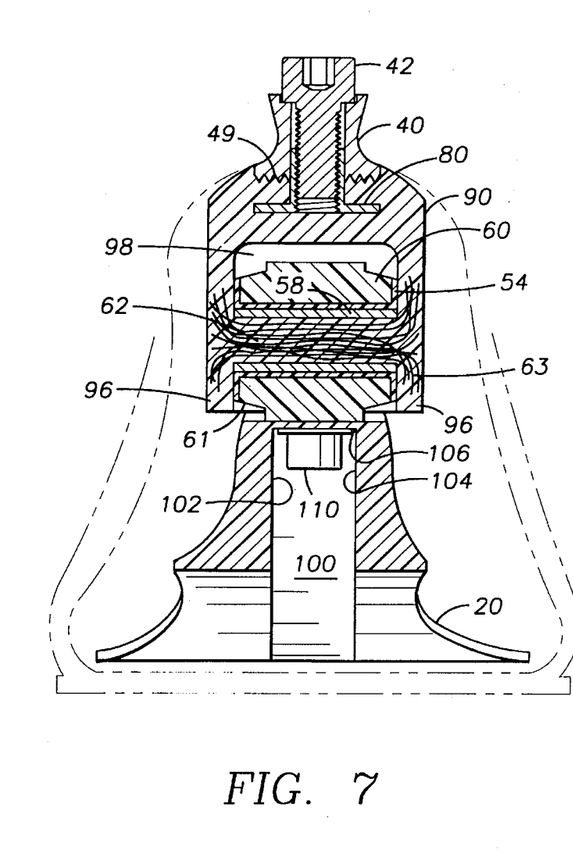
FIG. 7 is a cross-sectional view taken along lines 7—7 of FIG. 2.

Referring particularly to FIGS. 6 and 7, it will be seen that side portions 96 of shell 90 extend inwardly through bearing 58 to form integral axle 62 which extends through bearing 58. Forward and rear cups 92, 94 and side portions 96 of shell 90 enclose body 50, with side portions 96 being integral with axle 62. Between shell 90 and the top of body 50 is a void 98. The specific preferred method of construction of this joint is set forth in detail below.

Parallel to and proximate the position of liner 54 in body 60 are a forward transverse support 67 and a rear transverse support 68 passing through body 60 parallel to the x axis. A pair of threaded vertical bores 70, 72 also pass through body 50, intersecting transverse supports 67 and 68, respectively. For structural purposes, it is desired that the diameter of supports 67, 68 exceed the diameter of bores 70, 72. This ensures that a portion of each support extends beyond the bore, as shown.

Still referring to FIGS. 6 and 7, instep 24 of foot 20 includes a lower recess 100. Preferably, recess 100 comprises a longitudinal groove in instep 24 having side walls 102, 104 and an inner wall 106. As shown in FIGS. 5 and 6, vertical bores 23, 25 are located in inner wall 106.

Ankle joint 30 is attached to foot 20 by means of a pair of bolts 110, 112. Bolts 110, 112 pass through bores 23, 25, respectively and engage bores 70, 72, respectively, in body 50. It will be understood that bolts 110, 112 could be replaced with a single bolt, or other suitable attachment means. It is believed advantageous, however, to use at least two such attachment means, as it reduces fatigue in the attachment, even if the attachment(s) develop slack.

Referring now to FIGS. 5, 6 and 7, connector 40 is affixed to shell 90 by means of a T-nut 80 and a bolt 42. Connector 40 comprises an annular flange 44 adjacent one end of a coaxial four-sided body 47. The lower face of flange 44 preferably includes a plurality of longitudinal grooves 45 that run from the front to the back of the flange. Body 47 includes four curved faces 46 and a central bore 48 therethrough. Surrounding bore 48 is an annular recess 49, which is adapted to receive the head of bolt 42. T-nut 80 comprises a body 82 having a threaded bore 84 and a terminal flange 86, which supports four locking tabs (not shown). Preferably, T-nut 80, connector 40 and bolt 42 are made of metal and most preferably of steel. It has been found that 316 alloy steel is well suited to the present application.

Connector 40 is the male component of a standard adjustable connection formerly manufactured by the Otto Boch Corp. of West Germany and now widely available. Because of its strength and adjustability, this type of connection is presently used for virtually every non-flexible prosthetic connection.

According to a preferred embodiment, ankle joint 30 is constructed as follows. First, tubular bearing 58 is placed on a rigid cylindrical support having an outside diameter approximately equal to the inside diameter of bearing 58. Next, liner tubes 55 are placed over bearing 58, with their flanges at opposite ends thereof, to form liner 54. Tubes 55 are tightened around bearing 58 by wrapping them circumferentially with glass fiber so that expansion opening 56 is tightly closed.

Housing 60 is preferably formed around bearing 58 and liner 54 by winding unidirectional glass fiber circumferentially around the outside diameter of liner 54, and continuing the winding around adjacently positioned transverse supports 67, 68, resulting in a oblong housing shape that includes bevel 64 on each side. When the fiberglass of housing 60 has been positioned, a wax cast (not shown) is placed around the assembled housing components. The outer surface of the wax cast is sculpted to correspond to the desired contours of the inner surface of shell 90, including the contours of void 98 and the seats for snubbers 32, 34 in forward and rear cups 92, 94, respectively. The inner surface of the wax cast is sculpted to correspond to the desired contours of the outer surface of housing 60, including bevel 64. In this manner, the wax cast defines the void that will ultimately exist in joint 30 between housing 60 and shell 90.

Figure 6A:
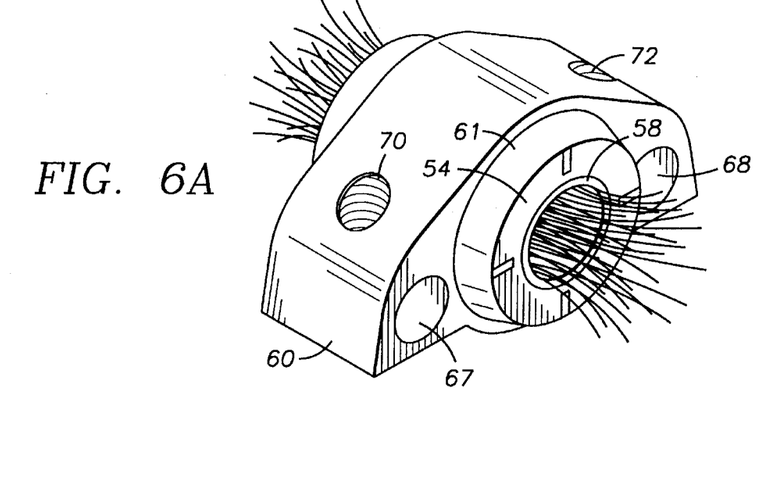
FIGS. 6A and 6B are perspective and front elevational views, respectively, of the joint of the present invention at an intermediate manufacturing step.
Figure 6B:
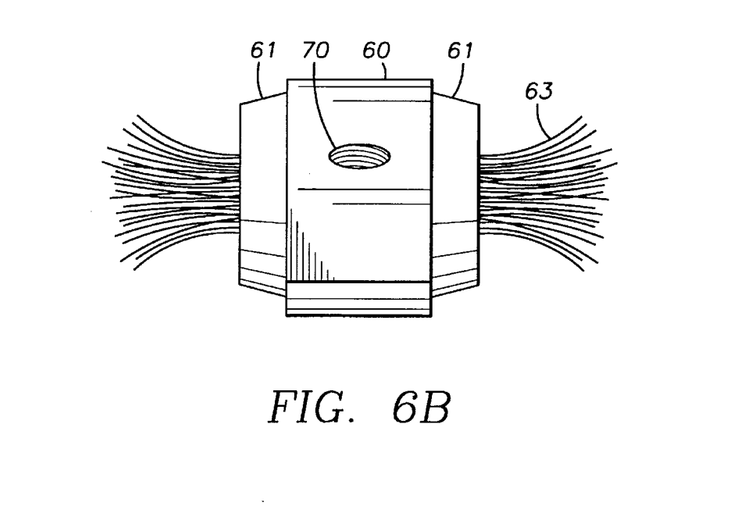

Axle 62 must be capable of withstanding significant shear stresses. Therefore, it is preferable that axle 54 be constructed of uniaxial glass fiber reinforced with epoxy, as best illustrated in FIGS. 6A and 6B. To achieve this, a plug 63 of unidirectional glass fiber is positioned in bearing 58 such that the ends of plug 63 extend a short distance beyond the ends of bearing 58 and beyond the sides of the wax cast. The ends of the glass fiber plug 63 are spread out, so that each end is slightly mushroom-shaped.

The dorsal surface of the wax cast is then wrapped in layers of additional fiberglass. Although the fibers of plug 63 forming axle 62 are shown in FIG. 7 for illustrative purposes, the additional fiberglass layers forming shell 90 are not shown. In the course of applying the fiberglass layers, T-nut 80 is incorporated into the top of shell 90. Preferably the fiberglass forming shell 90 includes the following layers:

| Position | No. of Layers | Weight of Fiber | Type of Glass | Orientation |
|---|---|---|---|---|
| 1 | 1 | 6 oz. | bidirectional | front to rear |
| 2 | 1 | 13 oz. | unidirectional | front to rear |
| 3 | 2 | 6 oz. | bidirectional | side to side |
| 4 | 2 | 26 oz. | unidirectional | side to side |
| 5 | 2 | 26 oz. | unidirectional | front to rear* |
| 6 | 1 | 26 oz. | unidirectional | transverse** |
| 7 | N/A | 52 oz. | mat | N/A*** |

*One layer ends in front of T-nut 80 and one passes over T-nut 80.
**This layer extends only across the front end 92 of shell 90.
***Glass mat is shaped to form the dome of joint 30, which serves to restrain T-nut 80 and provide support for a prosthetic leg connection.

Once all of the desired layers of fiberglass have been assembled around the wax cast, the fiberglass-wrapped cast is inserted into a mold, which is then sealed. The mold corresponds to the desired outer contours of shell 90, and includes grooves 99 running from front to back along the uppermost surface adjacent flanges 84 of T-nut 80. Grooves 99 in shell 90 correspond to grooves 45 in flange 44 of connector 40. Epoxy is drawn into the void between the east and the mold, including into bearing 58, thoroughly impregnating the fibers. Once the shell and axle have been thus formed, the joint is removed from the mold. The wax east is melted and removed, leaving joint 30 shown in FIG. 1 and described above, including integral axle 62. The flanges of liners 58 prevent housing 60 from being integrally joined to shell 90 and axle 62. A small amount of epoxy may flow between shell 90 and housing 60 through radial slots 57, but this amount is negligible and can be easily snapped to allow pivoting of the pieces relative to each other.

To affix connector 40 to shell 90, connector 40 is seated on T-nut 80 so that grooves 45 in flange 44 are seated in corresponding grooves 99 in shell 90 and prevent connector 40 from rotating or shifting laterally with respect to shell 90. Bolt 42 passes through connector 40 and threadingly engages bore 83 of T-nut 80.

Before foot 20 is connected to body 50, snubber 32 is positioned transversely within the forward cup 92 of shell 90 so that it rests on front contact surface 27, as best illustrated in FIG. 6. Snubber 32 is sized so that its diameter is approximately equal to the distance between contact surface 27 of instep 24 and the underside of forward cup 92 of shell 90. Because contact surface 27 is curved from side to side, only the center portion of forward snubber 32 contacts surface 27 in the normal, unflexed position.

Rear snubber 34 is positioned vertically within the rear cup 94 of shell 90 so that it rests on contact surface 29. Snubber 34 is sized so that its length is approximately equal to the distance between planar surface 29 of instep 24 and the underside of rear cup 94 of shell 90.

It has been found advantageous to provide ankle joint 30 in a plurality of sizes. Specifically, it has been found that three sizes are adequate to support the normal range of necessary prosthesis sizes. The size of axle 62 varies according to the desired prosthesis size; the 0.5 inch brass tubing disclosed above is suitable for a medium prosthesis. It is preferred that the height, or depth, of instep 24 be approximately 4%, 6%, or 8% of the length of foot portion 20 for small, medium and large prosthesis, respectively. This allows the cross-section perpendicular to the y axis of instep 24 to be great enough to provide the necessary rigidity through the middle of the foot, while maintaining the x axis (through bearing 58) as low as possible.

Figure 8:
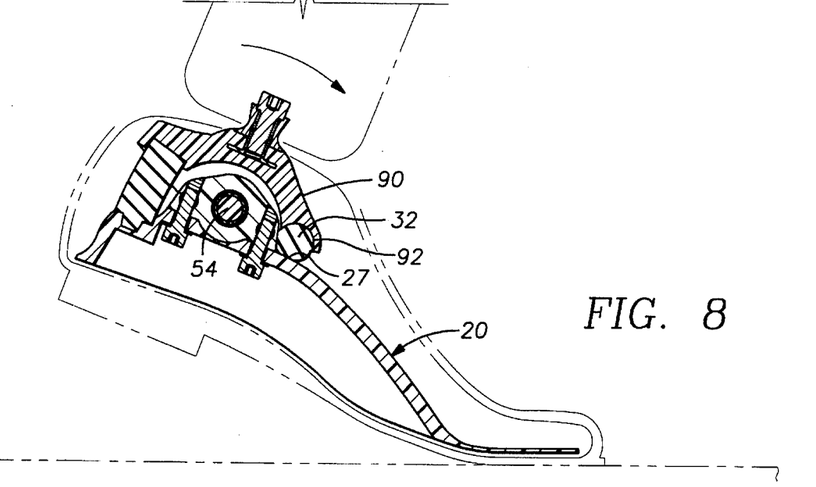
FIGS. 8–10 are sequential side elevational views of the foot of FIG. 1 showing motion of the foot and attached ankle joint through a step.

Referring now to FIG. 8, during dorsiflexion, the leg is inclined toward the front of the foot. Dorsiflexion occurs during the "push-off" phase of a normal step, or during uphill walking. In the prosthesis of the present invention, dorsiflexion causes a clockwise (as shown) moment about the x axis to be applied to shell 90. Because shell 90 is integral with axle 62, which is in turn bonded to bearing 58, bearing 58 rotates within liner 54 as shell 90 pivots. Pivoting of shell 90 causes front snubber 32 to be compressed between front contact surface 27 and forward cup 92. As the degree of flexion increases, snubber 32 deforms to fully contact the curved contact surface 27. Because snubber 32 is resilient and is substantially confined within forward cup 92, it resists compression and biases foot 20 away from forward cup 92. During normal use, a maximum dorsiflexion about axle 62 of approximately 10 to 15 degrees will occur.

For a given prosthesis size, the degree of dorsiflexion that can occur depends in part on the durometer, or hardness, of forward snubber 32. A desired durometer can be selected by modifying the composition of the snubber material. Methods for altering the durometer of a material, and of polymers in general are well known. If, as discussed above, Flexane® is used, an additive marketed under the trademark Flex-Add™ and also manufactured by Devcon, may be used to produce a softer polymer.

The radius of curvature r of contact surface 27 also affects the resistance of joint 30 to dorsiflexion. The smaller the radius of curvature r of contact surface 27, the smaller the area is of surface 27 that contacts snubber 32. With a smaller area, greater pressure will be applied by a given force, causing greater deformation. A surface 27 having a smaller radius of curvature will distort snubber 32 to a greater degree and allow more degrees of dorsiflexion with the same force. Thus, the same effect can be achieved by providing either a softer snubber or a smaller radius of curvature for contact surface 27.

The height of instep 24 can also affect the dorsal flexibility of the prosthetic foot. Because the flexibility of an object depends on its cross-section in the direction of flexure, raising the height of instep 24 produces a stiffer foot. Likewise, a more flexible foot can be produced by decreasing the height of instep 24. Because foot 20 is made of polypropylene in a preferred embodiment, it is capable of some flexure without breaking.

Figure 9:
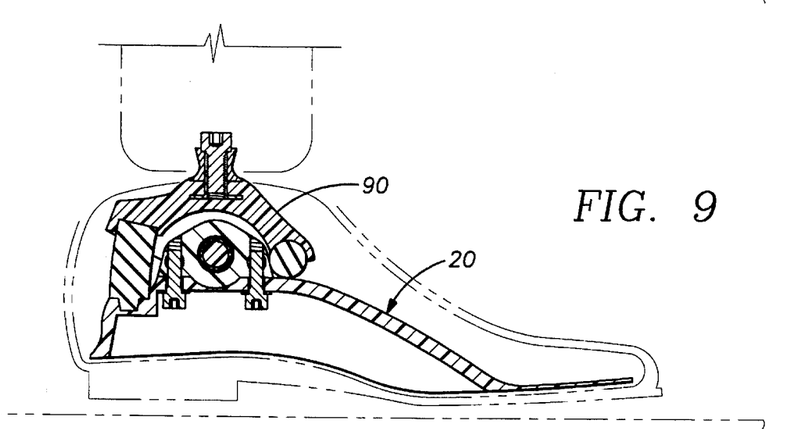

In contrast to instep 24, toe portion 26 of foot 20 has a small cross-sectional area, and therefore flexes relatively easily. Hence, as the wearer's body mass moves forward over the foot and begins to straighten the ankle, the energy stored in front snubber 32 is transferred into flexure of toe portion 26. When the toe of prosthesis 10 leaves the ground, moment is removed from the joint and prosthesis 10 returns to its unflexed position as the leg swings forward, as shown in FIG. 9. It is preferred that joint 30 store only a minimum amount energy, that amount being the amount necessary to return the prosthesis to its unflexed position. It is preferred that excess energy be dissipated within the resilient components of joint 30, so as to avoid an excessively bouncy step. The degree to which energy is dissipated, rather than being released, can be controlled by modifying the composition and structure of the resilient components.

Figure 10:
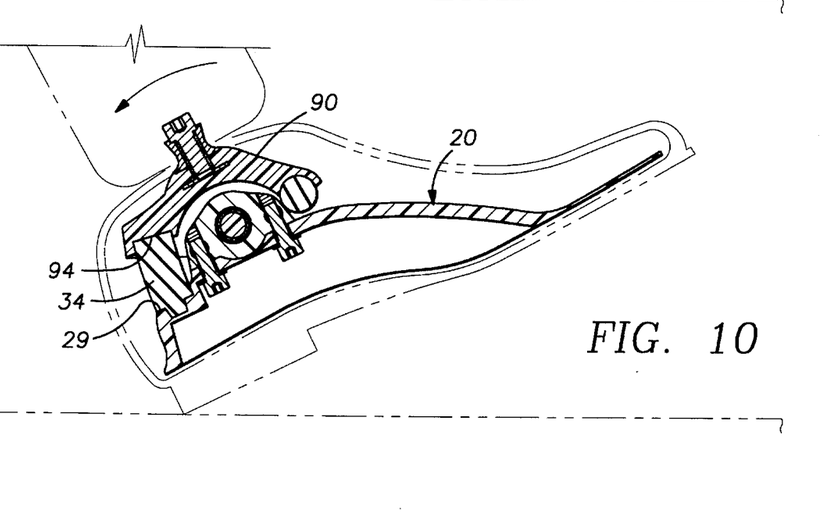

Referring now to FIG. 10, when the heel of prosthesis 10 is placed on the ground, a counter-clockwise moment is applied to the joint, resulting in planiflexion. As in dorsiflexion, shell 90 pivots, this time in a counter-clockwise direction about the x axis, causing bearing 58 to rotate liner 54. Rear snubber 34 is compressed between rear contact surface 29 of instep 24 and rear cup 94 of shell 90, and biases prosthesis 10 to return to an unflexed position. In addition, rear snubber 34 provides more shock-absorbing capability. Because it is oriented so that the compressive forces are applied along its longitudinal axis, it is capable of compression through a greater distance than the transversely mounted front snubber 32. During normal use, a maximum planiflexion about axle 62 of approximately 10 to 30 degrees will occur. Once the foot is planted, as the wearer moves forward the moment is removed and prosthesis 10 returns to an unflexed position before commencing the next push-off phase as shown in FIG. 10.

Another aspect of the present invention is the internal construction of cosmesis 28 itself. It has been found that the configuration of the "hard" portions of the present prosthesis, i.e., the foot and ankle joint, lend themselves particularly well to a cosmesis adapted to provide naturalistic cushioning as well as a semi-rigid instep suitable for supporting the laced upper of a shoe.

Figure 11:
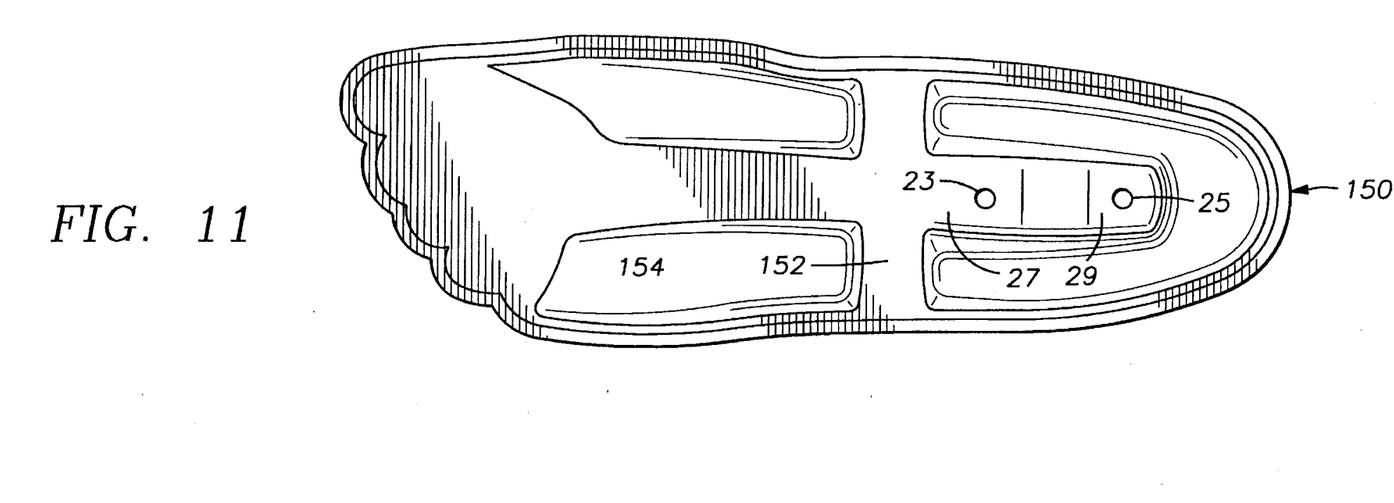
FIG. 11 is a plan view of the bottom half of a preferred cosmesis according to the present invention.
Figure 12:
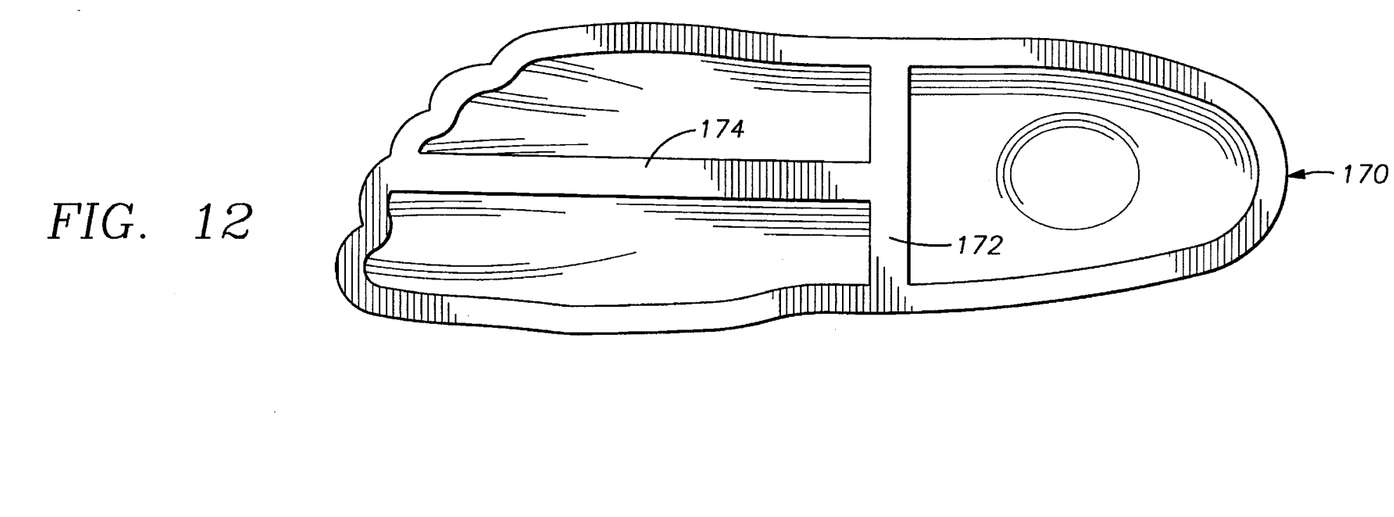
FIG. 12 is a bottom view of the top half of a preferred cosmesis according to the present invention.

Specifically, and as shown in FIG. 11, the present cosmesis comprises a pair of essentially hollow sections 150, 170, each with a wall thickness of about 0.25 inches. Plantar section 150 corresponds to the lower, or sole, portion of the foot and houses the hardware of the prosthesis. Section 150 is preferably molded around a foot portion 20, leaving the upper surfaces of foot 20 that support joint 30, namely contact surfaces 27, 29 and the concave mounting surface therebetween, exposed. Dorsal section 170 corresponds to the upper contours of the foot and may be designed to include simulations of such naturalistic features as toes and musculature on its outer surface. Fixed within each cosmesis sections 150, 170 are a transverse support 152, 172 and a sagittal support 154, 174. Longitudinal support 154 in lower section 150 coincides with and encases instep 24 of foot 20. Supports 152, 172 are transversely positioned just forward of front contact surface 27 and create a firmly supported instep that is suitable for receiving a lace-up shoe. Supports 152, 172 are aligned when the prosthesis is assembled. Sagittal supports 154, 174 extend perpendicularly forward from transverse supports 152, 172, and are also aligned when the prosthesis is assembled. Supports 152, 172 and 154, 174 are preferably formed from the same foamed material as cosmesis 28. While the supports can be molded into their respective sections 150, 170, it is easier to construct the supports separately and then insert and affix them into section 150, 170. As stated above, together supports 152, 172 and 154, 174 improve the operation and feel of the prosthesis.

An advantage of the joint of the present invention lies in the fact that it closely simulates the motion of an anatomical foot about the x axis while providing a lightweight, stable foot that is easily adapted to normal use.

What is claimed is:

1. A lightweight foot prosthesis, comprising:

a foot;

an ankle joint affixed to said foot and capable of rotation about a transverse axis, said joint comprising a body having a transverse bore therethrough and a shell, said shell including an integral axle extending through said bore such that said shell is pivotable with respect to said body, said axle and said shell being monolithic;

means for connecting said body to said foot; and means for connecting said shell to a leg.

2. The foot prosthesis according to claim 1 wherein said foot has a heel, a toe, and a raised instep.

3. The foot prosthesis according to claim 2 wherein said foot comprises a single piece of molded polymer.

4. The foot prosthesis according to claim 1 wherein said joint further includes a liner mounted between said body and said axle.

5. The foot prosthesis according to claim 4 wherein said joint further includes a bearing mounted between said body and said axle.

6. The foot prosthesis according to claim 5 wherein said axle is bonded to said bearing such that tilting of the shell causes said bearing to swivel within said liner.

7. The foot prosthesis according to claim 1, further including means for limiting rotation of said ankle joint.

8. The foot prosthesis according to claim 7 wherein said rotation limiting means is mounted between said shell and said foot.

9. The foot prosthesis according to claim 1 wherein said shell comprises a composite of glass fiber and epoxy.

10. The foot prosthesis according to claim 9 wherein said integral axle comprises glass fibers extending through and beyond said bore and impregnated with epoxy.

11. A light-weight foot prosthesis, comprising:
    a contoured one-piece foot having a flexible toe portion, a rigid instep, and a heel, said foot being molded of a light-weight copolymer;
    an ankle joint affixed to said foot and capable of rotation about the transverse axis, said joint comprising a body having a transverse bore therethrough and a shell surrounding said body, said shell including a monolithic axle extending through said bore such that said shell is pivotable with respect to said body;
    means affixed to said shell for connecting said ankle joint to a leg;
    means for connecting said body to said foot; and
    means for limiting rotation of said shell with respect to said foot.

12. The foot prosthesis according to claim 11 wherein said rotation limiting means comprises a pair of snubbers mounted between said foot and said shell.

13. The foot prosthesis according to claim 12 wherein said snubbers each comprise a cylinder constructed of a resilient material.

14. The foot prosthesis of claim 11, further including a cosmesis including dorsal and plantar sections, each section being sagittally and transversely internally supported.

15. The foot prosthesis of claim 14 wherein said plantar cosmesis section is adapted to support said foot.

16. The foot prosthesis of claim 14 wherein said dorsal cosmesis section is adapted to receive said joint.

* * * * *